United States Patent
Wandke et al.

(10) Patent No.: US 11,458,323 B2
(45) Date of Patent: Oct. 4, 2022

(54) PLASMA TREATMENT UNIT

(71) Applicant: CINOGY GMBH, Duderstadt (DE)

(72) Inventors: Dirk Wandke, Heiligenstadt (DE);
Mirko Hahnl, Berlingerode (DE);
Karl-Otto Storck, Duderstadt (DE);
Leonhard Trutwig,
Duderstadt/Gerblingerode (DE);
Melanie Ricke, Katlenburg-Lindau (DE)

(73) Assignee: CYNOGY GmbH, Duderstadt (DE)

( * ) Notice: Subject to any disclaimer, the term of this patent is extended or adjusted under 35 U.S.C. 154(b) by 408 days.

(21) Appl. No.: 16/639,391

(22) PCT Filed: Jul. 9, 2018

(86) PCT No.: PCT/DE2018/100625
§ 371 (c)(1),
(2) Date: Feb. 14, 2020

(87) PCT Pub. No.: WO2019/034198
PCT Pub. Date: Feb. 21, 2019

(65) Prior Publication Data
US 2020/0254270 A1    Aug. 13, 2020

(30) Foreign Application Priority Data

Aug. 15, 2017 (DE) .................... 10 2017 118 568.2

(51) Int. Cl.
*A61N 1/44* (2006.01)
*H05H 1/24* (2006.01)
(52) U.S. Cl.
CPC ............. *A61N 1/44* (2013.01); *H05H 1/2406* (2013.01); *H05H 1/2418* (2021.05)

(58) Field of Classification Search
CPC .. A61B 2018/00988; A61B 2090/0427; A61B 2090/0436; A61B 2090/0803;
(Continued)

(56) References Cited

U.S. PATENT DOCUMENTS

| 5,925,038 A | 7/1999 | Panescu et al. |
| 2013/0053762 A1 | 2/2013 | Rontal et al. |

(Continued)

FOREIGN PATENT DOCUMENTS

| DE | 102013019058 A1 | 5/2015 |
| DE | 102016100466 A1 | 7/2017 |

(Continued)

*Primary Examiner* — Monica C King
(74) *Attorney, Agent, or Firm* — WCF IP

(57) ABSTRACT

A plasma treatment unit having a high-voltage stage (5, 6), arranged in a housing, for generating high-voltage signals suitable for the generation of a plasma, and having a head part (2) which is connectable to the high-voltage stage (5, 6) and in which there is situated an electrode arrangement (13) shielded by a dielectric (9), is suitable for plasma treatments in particular in the body interior by virtue of the fact that the head part (2) has an elongate transition piece (10) which is attachable to the housing and on that end of which which is not connectable to the housing there is arranged a treatment head (16, 16'), the dimensions of which perpendicular to the longitudinal direction of the transition piece (10) greatly exceed the dimensions of the transition piece (10), and that, in the treatment head (16, 16'), the electrode arrangement (13) forms a spatially closed flexible sheath (12) around a resiliently elastic core (14) and is covered at its outer lateral surface by a thin layer (15) of the flexible dielectric (9), such that the treatment head (16, 16') can, as it is inserted into a body interior, assume the shape of the surrounding tissue in the body interior.

8 Claims, 4 Drawing Sheets

(58) Field of Classification Search
CPC ........... A61B 5/01; A61B 5/445; A61B 17/02; A61B 17/07207; A61B 17/1155; A61B 17/1285; A61B 17/320092; A61B 18/1477; A61B 2017/00017; A61B 2017/0003; A61B 2017/00039; A61B 2017/00061; A61B 2017/00075; A61B 2017/00123; A61B 2017/00128; A61B 2017/00154; A61B 2017/00176; A61B 2017/00199; A61B 2017/00203; A61B 2017/00221; A61B 2017/00367; A61B 2017/00393; A61B 2017/00398; A61B 2017/00424; A61B 2017/00464; A61B 2017/00473; A61B 2017/00482; A61B 2017/00725; A61B 2017/00734; A61B 2017/00818; A61B 2017/00938; A61B 2017/07214; A61B 2017/07228; A61B 2017/07235; A61B 2017/07271; A61B 2017/07285; A61B 2017/2903; A61B 2017/2927; A61B 2017/2929; A61B 2017/2931; A61B 2018/00166; A61B 2018/0041; A61B 2018/00422; A61B 2018/00494; A61B 2018/00517; A61B 2018/00541; A61B 2018/0063; A61B 2018/00994; A61B 2018/1861; A61B 2090/032; A61B 2090/035; A61B 2090/061; A61B 2090/064; A61B 2090/065; A61B 2090/0807; A61B 2090/0808; A61B 2090/0809; A61B 2090/0811; A61B 2090/0814; A61B 2090/392; A61B 2090/3937; A61B 2090/397; A61B 2217/005; A61B 2560/0219; A61B 2560/0252; A61B 2560/0418; A61B 2562/0238; A61B 2562/028; A61B 2562/12; A61B 3/0025; A61B 3/0058; A61B 3/10; A61B 3/1241; A61B 3/14; A61B 3/16; A61B 3/185; A61B 34/20; A61B 5/0002; A61B 5/031; A61B 5/14532; A61B 5/14546; A61B 5/14555; A61B 5/1486; A61B 5/18; A61B 5/412; A61B 5/416; A61B 5/4839; A61B 5/6814; A61B 8/06; A61B 90/96; A61B 90/98; A61B 1/00087; A61B 1/042; A61B 1/2736; A61B 17/0482; A61B 17/0625; A61B 17/0644; A61B 17/068; A61B 17/0682; A61B 17/072; A61B 17/083; A61B 17/105; A61B 17/12022; A61B 17/122; A61B 17/1222; A61B 17/1227; A61B 17/28; A61B 17/29; A61B 17/2909; A61B 17/32; A61B 17/320068; A61B 17/34; A61B 17/3421; A61B 18/082; A61B 18/245; A61B 2017/00115; A61B 2017/00119; A61B 2017/00269; A61B 2017/00327; A61B 2017/00544; A61B 2017/00752; A61B 2017/06076; A61B 2017/2901; A61B 2017/2923; A61B 2017/2936; A61B 2017/2943; A61B 2017/2944; A61B 2017/320044; A61B 2018/00005; A61B 2018/00017; A61B 2018/00023; A61B 2018/00077; A61B 2018/00095; A61B 2018/00113; A61B 2018/00261; A61B 2018/00267; A61B 2018/00285; A61B 2018/00303; A61B 2018/00315; A61B 2018/00351; A61B 2018/0044; A61B 2018/00482; A61B 2018/00488; A61B 2018/005; A61B 2018/00559; A61B 2018/00571; A61B 2018/00708; A61B 2018/00898; A61B 2018/1435; A61B 2018/1846; A61B 2018/1869; A61B 2018/1892; A61B 2034/2048; A61B 2034/2059; A61B 2034/254; A61B 2034/256; A61B 2034/258; A61B 2034/305; A61B 2090/066; A61B 2090/3614; A61B 2090/365; A61B 2090/372; A61B 2090/373; A61B 2090/3735; A61B 2090/3983; A61B 2090/502; A61B 2217/007; A61B 2218/005; A61B 2562/0209; A61B 2562/0257; A61B 2562/0261; A61B 34/25; A61B 34/30; A61B 34/35; A61B 34/37; A61B 34/71; A61B 34/74; A61B 5/0022; A61B 5/02042; A61B 5/14542; A61B 5/24; A61B 5/287; A61B 5/6847; A61B 90/37; A61B 90/53; A61B 90/92; H05H 1/2406; H05H 1/2418; H05H 2245/30; H05H 2240/20; H05H 2277/10; H05H 2245/60; H05H 1/26; H05H 1/46; H05H 2240/10; H05H 2245/32; H05H 2245/36; H05H 1/466; H05H 1/24; H05H 1/4697; H05H 1/48; H05H 1/2425; H05H 1/2437; H05H 1/471; H05H 2242/00; H05H 1/2481; H05H 1/2431; H05H 1/2475; H05H 1/34; H05H 1/30; H05H 1/3484; H05H 13/04; H05H 2245/34; H05H 7/10; H05H 1/246; H05H 1/2465; H05H 1/3423; H05H 1/3431; H05H 1/3447; H05H 1/44; H05H 2245/15; H05H 2245/40; A61N 1/44; A61N 2/02; A61N 2/06; A61N 1/0551; A61N 1/36117; A61N 2007/003; A61N 5/1002; A61N 7/022; A61N 1/0468; A61N 2/006; A61N 1/0472; A61N 1/3603; A61N 1/40; A61N 2/002; A61N 1/0412; A61N 1/0444; A61N 1/0456; A61N 1/325; A61N 1/327; A61N 1/36014; A61N 1/403; A61N 2/004; A61N 2/008; A61N 5/10; A61N 1/0424; A61N 1/0428; A61N 1/328; A61N 2005/0641; A61N 2005/1067; A61N 5/1064; A61N 5/1081; A61N 1/0408; A61N 1/044; A61N 1/14; A61N 1/16; A61N 1/322; A61N 2/00; A61N 2005/1011; A61N 7/00

See application file for complete search history.

(56) References Cited

U.S. PATENT DOCUMENTS

| | | |
|---|---|---|
| 2016/0128769 A1 | 5/2016 | Rontal et al. |
| 2016/0361558 A1 | 12/2016 | Jacofsky et al. |
| 2017/0128127 A1 | 5/2017 | Skalnyi |
| 2019/0247050 A1* | 8/2019 | Goldsmith ....... A61B 17/12181 |

FOREIGN PATENT DOCUMENTS

| | | |
|---|---|---|
| EP | 1628688 B1 | 3/2006 |
| WO | 2010103262 A1 | 9/2010 |

* cited by examiner

PLASMA TREATMENT UNIT

The invention relates to a plasma treatment unit having a high-voltage stage arranged in a housing for generating high-voltage signals suitable for the generation of a plasma and a head part connectable to the high-voltage stage, in which an electrode arrangement shielded by a dielectric layer is located.

Such a plasma treatment unit is known from DE 10 2013 019 058 or US 2016/0242269 A1. In this case, this is a plasma treatment unit, in which the housing forms a handle part, on which a head part having a ball electrode is located. The ball electrode is formed as a rigid ball on an electrically conductive material, specifically metal, and is shielded at least over the largest part of the ball surface using a thin layer made of a dielectric material. The unshielded part of the spherical electrode is located inside the housing section of the head part, from which the spherical electrode only protrudes with a small ball section. The plasma treatment unit is used to be able to be rolled with the spherical electrode on a surface, to thus be able to treat a larger surface gradually using the plasma field generated by the ball electrode.

Furthermore, electrode arrangements are known from EP 1 628 688 B1, which are formed rod-shaped to be able to be inserted into, for example, an oral cavity in order to perform a dental treatment therein, for example. For this purpose, the electrode arrangement has to be substantially smaller than the oral cavity.

The invention is based on the object of designing a plasma treatment unit of the type mentioned at the outset in such a way that novel areas of application for the plasma treatment are enabled.

To achieve this object, according to the invention, a plasma treatment unit of the type mentioned at the outset is characterized in that the head part comprises an oblong transition part attachable to the housing, to the end thereof which is not connectable to the housing a treatment head is arranged, the dimensions of which perpendicular to the longitudinal direction of the transition part significantly exceed the dimensions of the transition part, and in the treatment head, the electrode arrangement forms a spatially closed flexible envelope around a soft-elastic core and is covered on its outer lateral surface by a thin layer of the flexible dielectric material, so that the treatment head, upon insertion into a body interior can assume the shape of the surrounding tissue in the body interior.

It is possible by way of the plasma treatment unit having the treatment head designed according to the invention to also carry out a plasma treatment in the body interior with a high efficiency. Due to the spatially closed flexible envelope formed by the electrode arrangement and the coverage of this flexible envelope to the outside by a flexible dielectric material, the treatment head can adapt itself to various conditions in various body cavities and passages. Thus, for example, a plasma treatment in the auditory canal is possible to cause wound surfaces present therein, for example, after an ear operation, to heal more rapidly. Furthermore, inflammatory processes in the auditory canal can be treated by the treatment head, the external dimensions of which are larger than those of the auditory canal, being inserted into the auditory canal, whereby the treatment head assumes the shape of the auditory canal.

A treatment of the mucous membrane inside the nasal passages can be performed in a similar manner.

Furthermore, treatments in naturally existing body cavities and canals passages of any type, for example, in the rectum, can be performed using the plasma treatment unit according to the invention. However, the treatment in the body interior through artificial accesses, as are placed in the case of minimally invasive operations, is also possible. The transition part of the head part can accordingly be formed flexibly in particular and can have different lengths. In particular, the transition part to the treatment head can have a form similar to wire or tubing.

It is furthermore preferable that the housing is formed as a handle part, using which the head part is replaceably connectable to the treatment head according to the invention. The head part can preferably also be sterilely packaged as a single-use treatment head to be disposed of harmlessly after the treatment. The expenditure for a sterilization, which is critical in many cases, can therefore be omitted.

A starting shape for the treatment head as a ball or as a truncated cone is preferred. However, other starting shapes are also possible, such as cylindrical shapes having round or polygonal cross section, cube shapes of different sizes, etc.

It is advantageous for the treatment head according to the invention if the electrode arrangement is formed by a castable plastic layer, which has been made conductive by conductive additives. The plastic of the electrode arrangement can be of the same type as the dielectric material in this case, so that the electrode arrangement are connected easily in a materially bonded manner to the dielectric material.

The soft-elastic core preferably consists of a soft-elastic plastic foam or a soft-elastic gel. The formation of the soft-elastic core by an enclosed air or gas volume would also be conceivable.

Since the dielectric material covering the lateral surface of the electrode arrangement presses against tissue to be treated as much as possible over the entire surface, it is advantageous if the outer surface of the dielectric material comprises an external structure which forms free spaces for the formation of plasma upon application to walls in the body interior. The outer structure can be formed in this case by nubs acting as spacers, by a grid structure, or the like.

The electrode arrangement can consist of a single closed electrode layer, which is supplied with the high-voltage signals and for which the body to be treated functions as a (floating) counter electrode. However, the electrode arrangement can also form two electrodes, for example, by way of strips interleaved with one another, which are preferably fed with counter phase high-voltage signals of equal amplitude, so that the surrounding tissue still functions as a counter electrode or reference electrode, but due to the two electrodes, a resulting null voltage having spacing from the plasma formed always results.

It is furthermore possible to supply the two electrodes in such a way that one receives the high-voltage signal and the other is at a reference potential. In this case, the plasma treatment is not carried out as efficiently as upon the use of the body as the counter electrode. In the individual case, however, it can be reasonable to operate the plasma treatment unit itself using a reference potential.

A preferred material in each case for the electrode arrangement and for the dielectric material is a silicone, which has dielectric properties, but which can be made conductive for the electrode arrangement by conductive particles.

The invention will be explained in greater detail hereafter on the basis of exemplary embodiments illustrated in the drawing. In the figures:

FIG. 1 shows a first exemplary embodiment of a plasma treatment unit in four illustrations wherein FIG. 1*a*) shows a side view of three unit parts which are not yet assembled, FIG. 1*b*) shows a top view of the assembled unit, FIG. 1*c*) shows a view (from the opposite side with respect to FIG. 1*a*)), and FIG. 1*d*) shows a section through the assembled unit along section line A-A in FIG. 1*b*).

Figure 1:
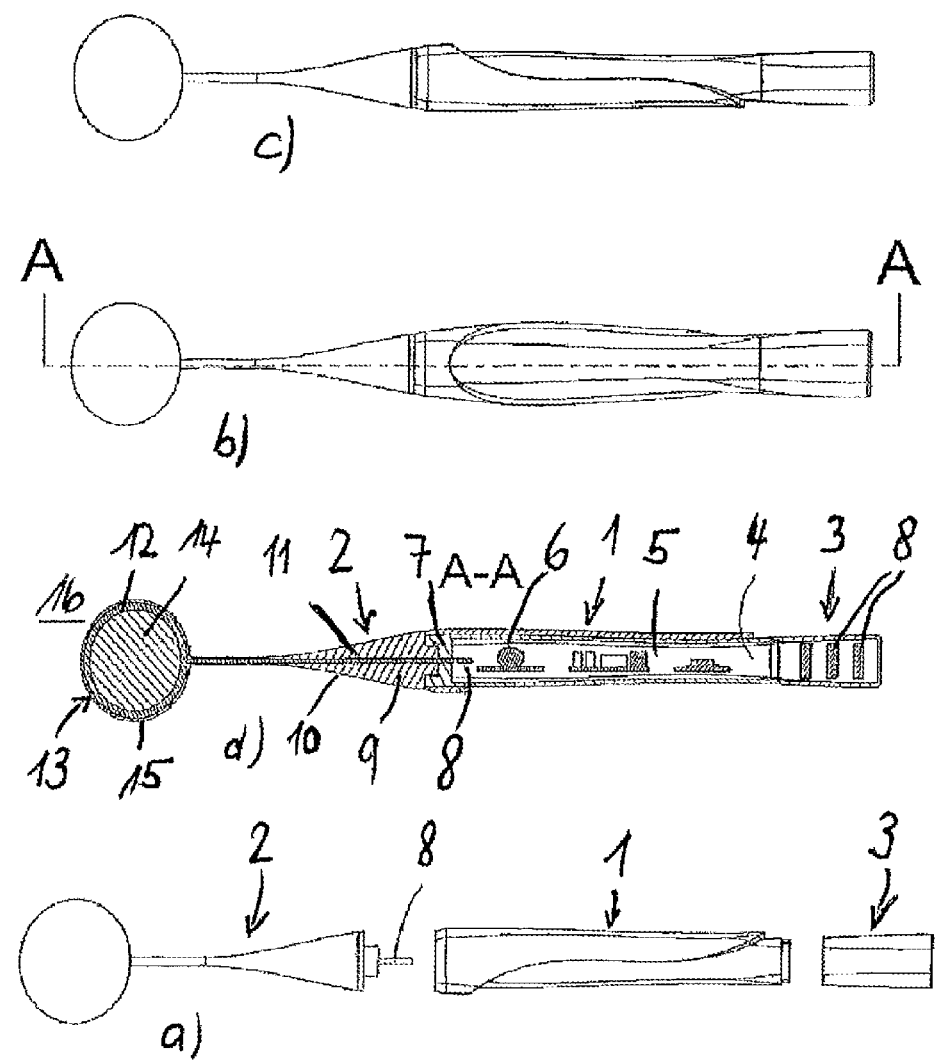
FIG. 1 shows illustrations of a plasma treatment unit having a treatment head in ball form.

The illustrated plasma treatment unit consists of a handle part 1, a head part 2, and a rear terminus part 3. The connections between handle part 1 and head part 2 and also between handle part 1 and rear terminus part 3 are preferably snap connections, but can also be formed, however, as screw connections, bayonet connections, or the like. The handle part 1 comprises a slightly ergonomically formed outer contour, which is to enable the secure gripping of the plasma treatment unit. The hollow handle part 1 comprises an interior 4, in which an electronic controller 5 is located, which generates AC voltage pulses from a DC voltage, which are converted using a coil arrangement 6 into high-voltage pulses. The high-voltage pulses reach a bushing (not shown in greater detail) inserted into a terminus part 7, which is insulating on the end face, via which the generated high-voltage pulses can be transmitted to the head part 2.

The rear terminus part 3 encloses three batteries 8, which are easily accessible and replaceable by removing the rear terminus part 3. The illustrated exemplary embodiment therefore represents a handheld unit which manages without a supply cable and can therefore be handled conveniently. However, it is also conceivable in the scope of the invention to supply the unit with a power supply via a cable, wherein the power supply can be a DC voltage supply or an AC voltage supply, for example, from the public power network. In the latter case, the controller 5 expediently contains a rectifier and chopper stage.

The head part protrudes with a connecting pin 8 out of the head part and into the bushing of the terminus part 7 of the handle part 1. In the head part 2, a dielectric material 9 forms a transition part 10, which encloses a wire-shaped electrode part 11 in an insulating manner. The wire-shaped electrode part 11 merges within a treatment head adjoining the transition part 10 into a spherical, closed envelope 12, so that an electrode arrangement 13 is formed by the wire-shaped electrode section 11 and the hollow envelope 12. The envelope 12 encloses a soft-elastic core 14, for example made of a soft-elastic foam, a soft-elastic gel, or the like. The envelope 12 of the electrode arrangement 13 is completely enclosed by a closed layer 15 of the dielectric material 9, so that only a dielectric barrier plasma discharge can always form by way of the electrode arrangement 13, in which no resulting current flow is possible from the electrode arrangement 13 to a counter electrode. The layer 15 can comprise a structure (not shown) on its surface, due to which air or gas spaces remain between the surface of the layer 15 and the surrounding tissue, in which the plasma can arise.

Because of the soft-elastic core 14, the thin flexible envelope of the electrode arrangement 13, and the flexible dielectric outer layer 15, the treatment head 16 thus formed is easily deformable and can adapt itself without problems to the shape of a body cavity or a body passage. In this manner, an intensive plasma treatment takes place in the region of the tissue to which the treatment head 16 is applied.

Figure 2:
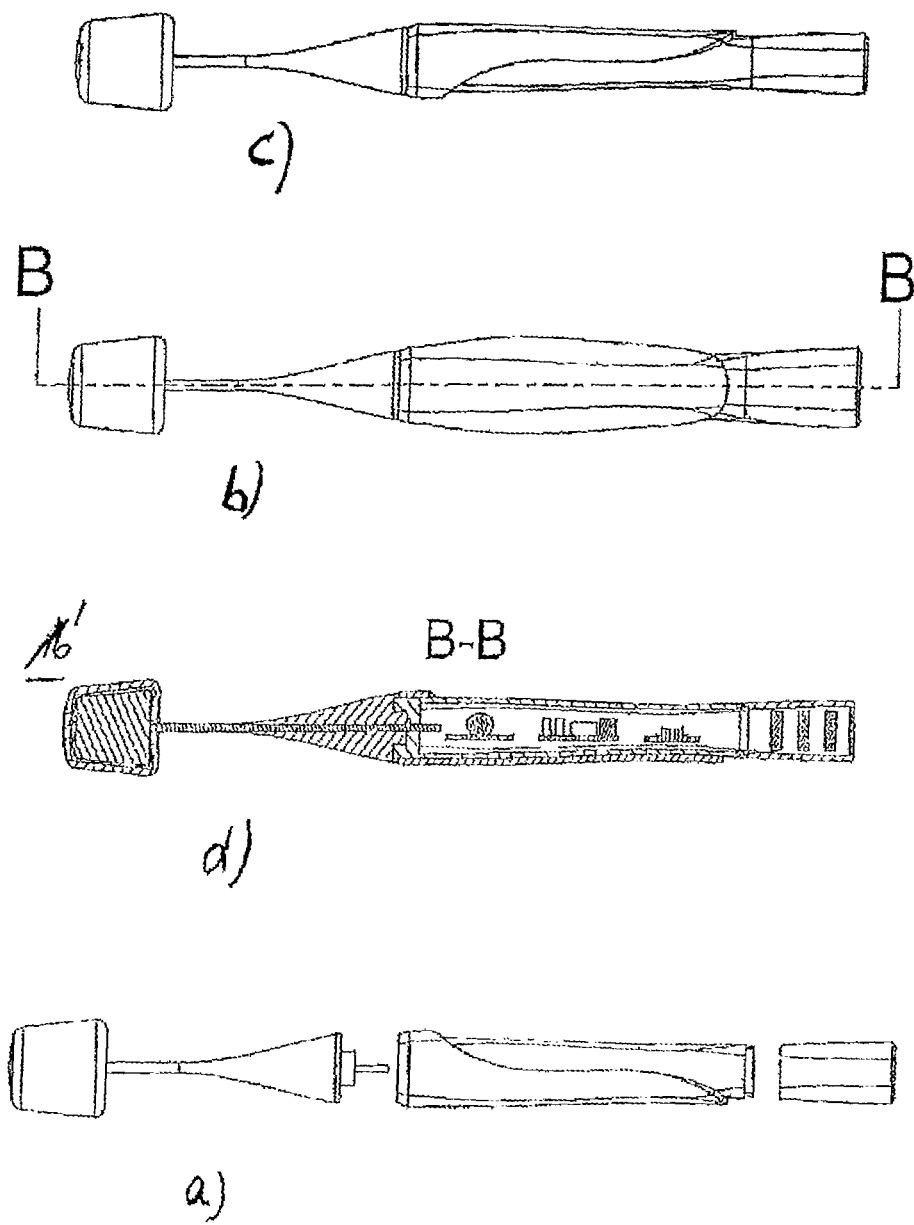
FIG. 2 shows illustrations as in FIG. 1 for the plasma treatment unit, in which the treatment head is deformed into a truncated cone by an insertion into a body cavity.

FIG. 2 shows an identical embodiment, in which a treatment head 16' constructed in the same structure has a starting shape in the shape of a truncated cone. This shape of the treatment head 16' is particularly suitable for the introduction into body passages, such as auditory canal or nasal passage.

Figure 3:
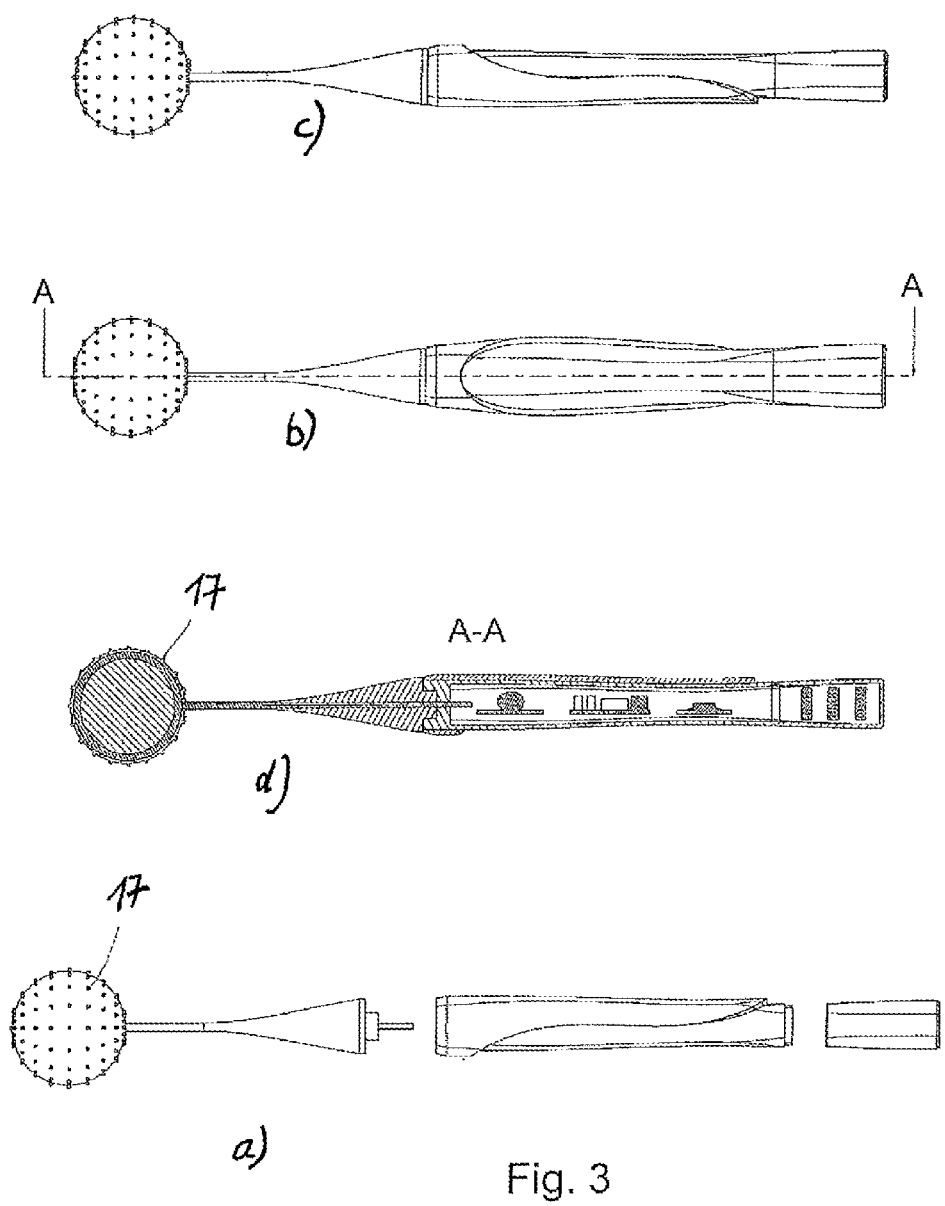
FIG. 3 shows illustrations according to FIG. 1 for a plasma treatment unit, in which the treatment head in ball form comprises spacers in the form of knobs on its outer side.

The plasma treatment unit illustrated in FIG. 3 is formed identically to the plasma treatment unit according to FIG. 1, but the spherical envelope 12 comprises spacers 17 on its outer side, which are formed here in the form of nubs. The spacers 17 have the function of ensuring an air space between the body tissue and the envelope 12, in which the dielectric barrier plasma can be generated by the electrode arrangement 13.

The spacers 17 are arranged distributed uniformly over the entire ball surface of the envelope 12. The head part 2 is thus usable universally. For special applications, it can also be reasonable to use a head part 2 in which the spacers 17 are only arranged in sections on the surface of the envelope 12.

Figure 4:
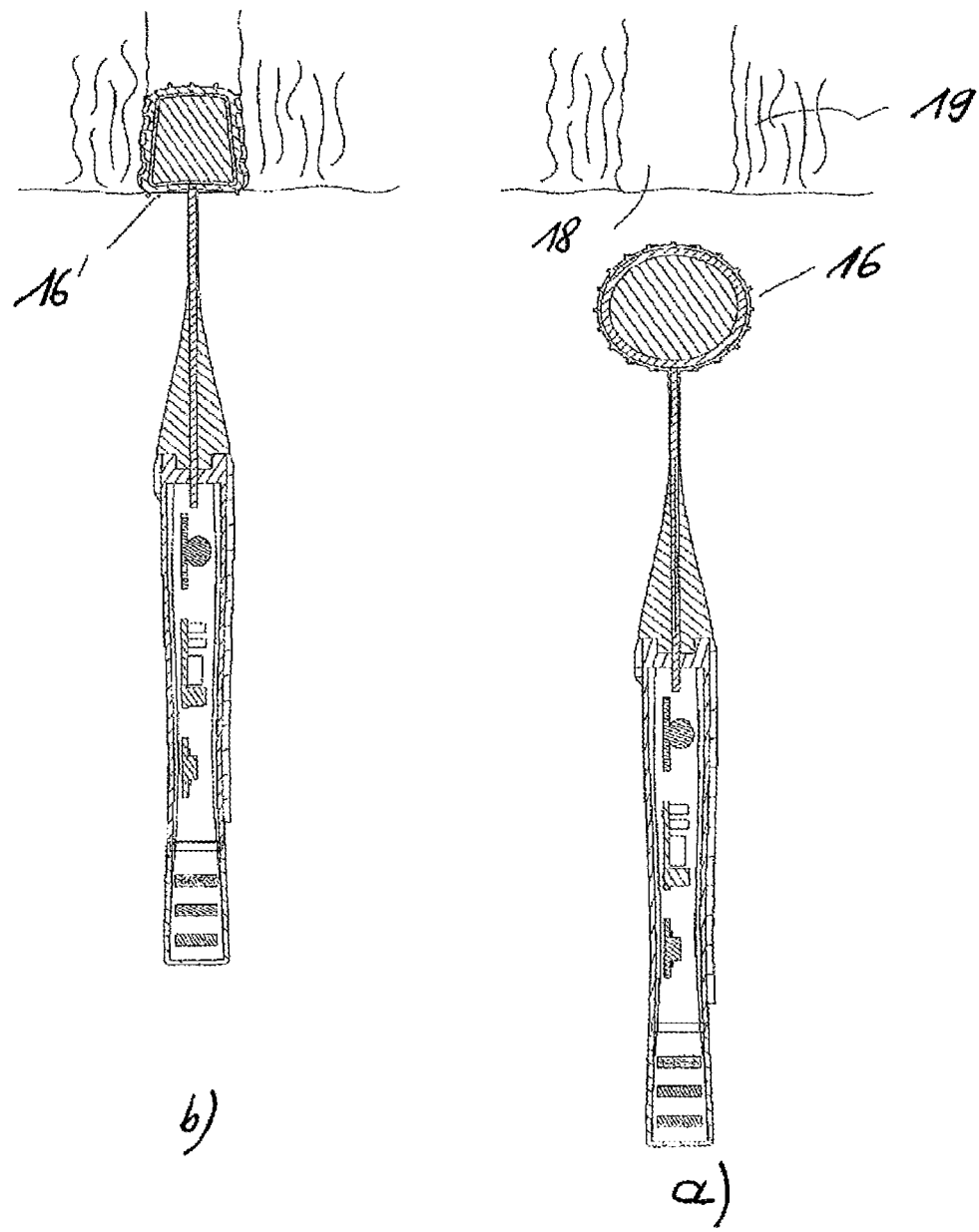
FIG. 4 shows the plasma treatment unit according to FIG. 3 before the insertion into a body cavity (FIG. 4*a*)) and after the insertion into a body cavity (FIG. 4*b*)).

FIG. 4 shows the plasma treatment unit according to FIG. 3 before the introduction into a body opening 18, which is enclosed by a body tissue 19. The body opening 18 can be a natural body opening, such as an auditory canal, a nasal opening, a rectal opening, or the like, but can also be an artificial opening or an artificial access in the form of a catheter or an operation incision. FIG. 4*b*) illustrates in this case that the envelope 12, which is in the form of a hollow ball in the rest state, is deformed by the pressing in of the head part 2, so that, for example, as shown in FIG. 4*b*), it assumes a truncated cone shape, to thus produce a large-area contact with the surrounding tissue 19, which in this manner can be intensively treated using the dielectric barrier plasma forming in the intermediate spaces between the spacers 17. In this manner, for example, operatively applied accesses, operation incisions, or the like may be treated to counteract infections in this region, to stimulate the microcirculation of the tissue 19 in the region of the body opening 18, and to accelerate the healing process for the operation wound.

The invention claimed is:

1. A plasma treatment unit, comprising:
   a high-voltage stage arranged in a housing for generating high-voltage signals suitable for the generation of a plasma;
   a head part connectable to the high-voltage stage;
   an electrode arrangement shielded by a dielectric material located in the head part,
   wherein the head part comprises an oblong transition part attachable to the housing,
      a treatment head being arranged at an end of the head part which is not connectable to the housing, the treatment head having dimensions perpendicular to a longitudinal direction of the transition part which exceed dimensions of the transition part, and
   wherein the electrode arrangement forms a spatially closed flexible envelope around a soft-elastic core and is covered on an outer lateral surface by a thin layer of the flexible dielectric material so that the treatment head, upon insertion into a body interior, assumes a shape of surrounding tissue in the body interior.

2. The plasma treatment unit as claimed in claim 1, wherein the thin layer of the dielectric material comprises an outer structure which forms free spaces for formation of a plasma upon application to the body interior.

3. The plasma treatment unit as claimed in claim 1 wherein the transition part is flexible.

4. The plasma treatment unit as claimed in claim 1 wherein the transition part the treatment head is wire shaped.

5. The plasma treatment unit as claimed in claim 1 wherein the transition part to the treatment head is tubular in shape.

6. The plasma treatment unit as claimed in claim 1 wherein the housing is formed as a handle part to which the head part is replaceably connectable.

7. The plasma treatment unit as claimed in claim 1 wherein the treatment head is ball shaped.

8. The plasma treatment unit as claimed in claim 1 wherein the treatment head has a truncated cone shape.

\* \* \* \* \*